United States Patent
Inoue

(10) Patent No.: US 11,540,699 B2
(45) Date of Patent: Jan. 3, 2023

(54) MEDICAL MANIPULATOR SYSTEM

(71) Applicant: Olympus Corporation, Hachioji (JP)

(72) Inventor: Shintaro Inoue, Cambridge, MA (US)

(73) Assignee: OLYMPUS CORPORATION, Tokyo (JP)

( * ) Notice: Subject to any disclaimer, the term of this patent is extended or adjusted under 35 U.S.C. 154(b) by 920 days.

(21) Appl. No.: 16/269,253

(22) Filed: Feb. 6, 2019

(65) Prior Publication Data

US 2019/0167079 A1 Jun. 6, 2019

Related U.S. Application Data

(63) Continuation of application No. PCT/JP2016/087144, filed on Dec. 14, 2016.

(51) Int. Cl.
*A61B 1/00* (2006.01)
*A61B 1/313* (2006.01)
(Continued)

(52) U.S. Cl.
CPC ...... *A61B 1/00149* (2013.01); *A61B 1/00006* (2013.01); *A61B 1/0016* (2013.01);
(Continued)

(58) Field of Classification Search
CPC ............ A61B 1/00149; A61B 1/00006; A61B 1/00055; A61B 1/0016; A61B 1/3132;
(Continued)

(56) References Cited

U.S. PATENT DOCUMENTS

| | | |
|---|---|---|
| 2013/0035697 A1 | 2/2013 | Ogawa et al. |
| 2013/0041219 A1 | 2/2013 | Hasegawa et al. |
| 2013/0066333 A1 | 3/2013 | Hyodo |
| 2013/0116706 A1* | 5/2013 | Lee ........................ A61B 34/76 606/130 |
| 2014/0135795 A1 | 5/2014 | Yanagihara |
| 2014/0144258 A1 | 5/2014 | Kishi |

(Continued)

FOREIGN PATENT DOCUMENTS

| | | |
|---|---|---|
| JP | 7-68480 | 3/1995 |
| JP | 8-215205 | 8/1996 |

(Continued)

OTHER PUBLICATIONS

International Search Report and Written Opinion from corresponding International Application No. PCT/JP2016/087144, dated Mar. 14, 2017.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

The technology disclosed herein is directed to a medical manipulator system having a medical device. The medical device such as endoscope or other surgical instrument includes an elongated insertion portion. A holder assembly includes an articulated arm carrying the medical device that is attached thereto and is actuated following movement of the medical device and holds the medical device in a stationary state at a desired position. A position/attitude detection unit detects positions and attitudes of the elongated insertion portion in plurality states into which the medical device is caused to swing about a constraint point. A constraint point estimation unit estimates a position of the constraint point based on the positions and attitudes of the (Continued)

insertion portion as detected by the position/attitude detection unit.

10 Claims, 7 Drawing Sheets

(51) Int. Cl.
  *A61B 34/20* (2016.01)
  *A61B 5/06* (2006.01)
  *A61B 34/30* (2016.01)
  *B25J 13/08* (2006.01)
  *A61B 34/00* (2016.01)
  *A61B 90/00* (2016.01)

(52) U.S. Cl.
  CPC ........ *A61B 1/00055* (2013.01); *A61B 1/3132* (2013.01); *A61B 5/065* (2013.01); *A61B 34/00* (2016.02); *A61B 34/20* (2016.02); *A61B 34/30* (2016.02); *B25J 13/088* (2013.01); *A61B 2034/2059* (2016.02); *A61B 2090/067* (2016.02)

(58) Field of Classification Search
  CPC ......... A61B 34/00; A61B 34/20; A61B 34/30; A61B 5/065; A61B 2034/2059; A61B 2090/067; B25J 13/088
  See application file for complete search history.

(56) References Cited

U.S. PATENT DOCUMENTS

| | | |
|---|---|---|
| 2014/0148817 A1 | 5/2014 | Hasegawa et al. |
| 2014/0148818 A1 | 5/2014 | Komuro et al. |
| 2014/0148819 A1 | 5/2014 | Inoue et al. |
| 2014/0148820 A1 | 5/2014 | Ogawa et al. |
| 2014/0148821 A1 | 5/2014 | Nakayama |
| 2014/0148950 A1 | 5/2014 | Ogawa et al. |
| 2014/0160015 A1 | 6/2014 | Ogawa et al. |
| 2014/0166023 A1 | 6/2014 | Kishi |
| 2014/0195052 A1* | 7/2014 | Tsusaka ............... B25J 3/04 700/260 |
| 2017/0367774 A1 | 12/2017 | Scholan |

FOREIGN PATENT DOCUMENTS

| | | |
|---|---|---|
| JP | 2006-312079 | 11/2006 |
| JP | 2013-34862 | 2/2013 |
| WO | 2015158756 | 10/2015 |
| WO | 2016071674 | 5/2016 |

* cited by examiner

MEDICAL MANIPULATOR SYSTEM

CROSS-REFERENCE TO RELATED APPLICATION

This application is a continuation application of PCT Application No. PCT/JP2016/087144 filed on Dec. 14, 2016, which is hereby incorporated by reference in its entirety.

TECHNICAL FIELD

The technology disclosed relates to a medical manipulator system.

DESCRIPTION OF THE RELATED ART

There are known medical manipulators related to an arm that holds an insertable device such as an endoscope at a tip of the medical manipulator as disclosed in a Japanese Patent Application JP 2006-312079A.

In such a medical manipulator, to instruct a user the position of an insertion hole formed in the body wall of a patient to permit insertion of the insertable device, a dedicated jig is used and held in place of the insertable device at the tip of the arm so as to provide an indication of the position of the insertion hole.

However, one drawback of the medical manipulator disclosed by Japanese Patent Application JP 2006-312079A is that the dedicated jig is needed to teach the position of the insertion hole. Another drawback of the aforementioned medical manipulator is that an instruction method of the insertion hole is required to use the dedicated jig. Moreover, there is also a problem in that, if the position of the insertion hole happens to move relative to reference coordinates of the medical manipulator during treatment of a patient, then needs arise to once pull out the insertable body from the insertion hole, to attach back the dedicated jig, and then to carry out teaching work.

BRIEF SUMMARY OF EMBODIMENTS

In an aspect of the technology disclosed, a medical manipulator system includes a medical device, a holder assembly, a sensor, and a first controller. The medical device includes an elongated insertion portion. The holder assembly has an articulated arm carrying the medical device attached thereto. The holder assembly is actuated following movement of the medical device and can hold the medical device in a stationary state at a desired position. The sensor is configured to detect positions and attitudes of the elongated insertion portion in plurality states into which the medical device is caused to swing about a predetermined constraint point. The first controller is configured to estimate a position of the constraint point based on the positions and attitudes of the insertion portion as detected by the sensor.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
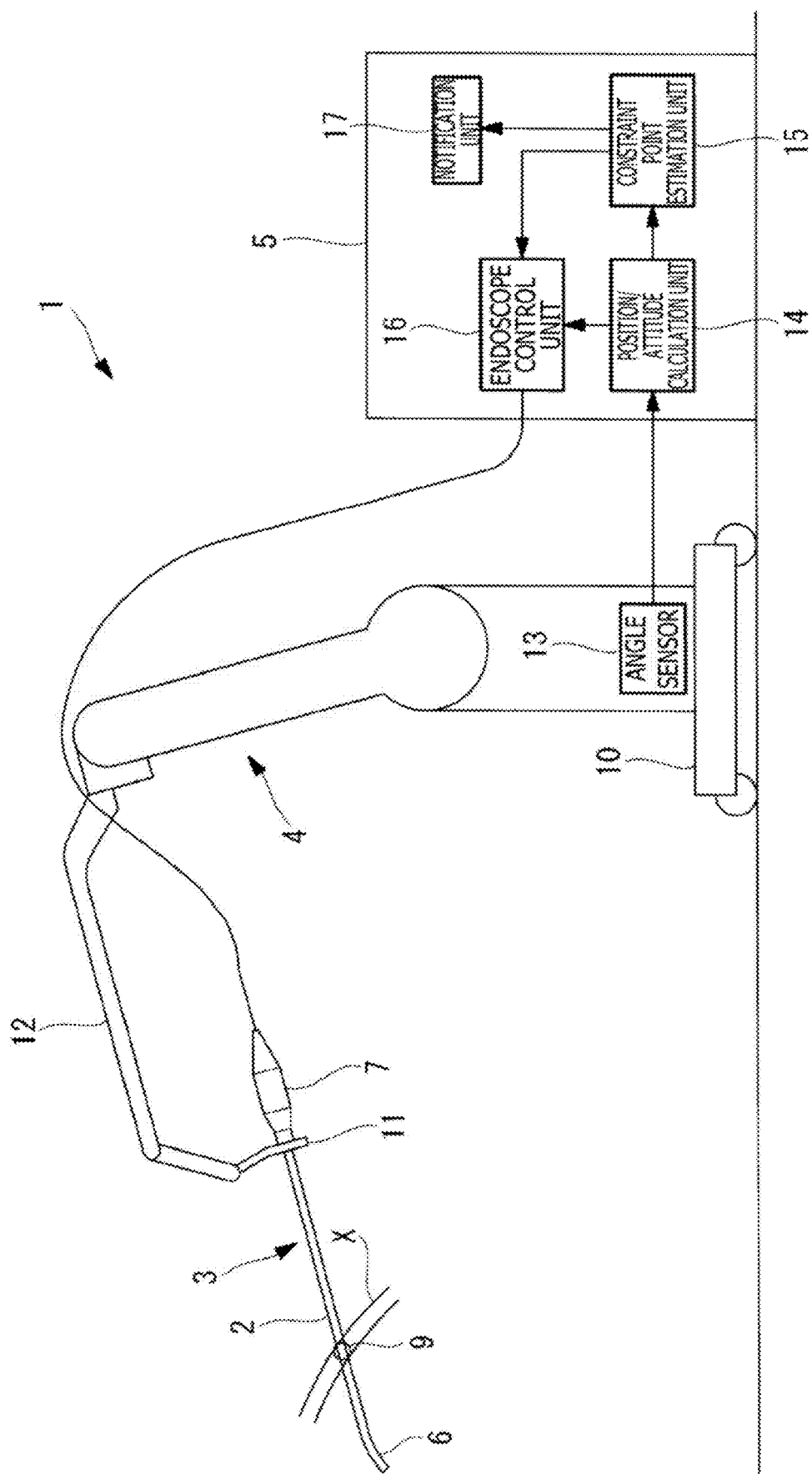
FIG. 1 is a schematic diagram depicting a medical manipulator system according to an embodiment described herein.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has as an object thereof the provision of a medical manipulator system that can correct movement of an insertion hole relative to reference coordinates of a medical manipulator without using any dedicated jig while maintaining an insertion portion of a medical device in a state of being kept inserted in the insertion hole.

In an aspect of the technology disclosed, a medical manipulator system includes a medical device, a holder assembly, and a control unit all of which are attached to one another to permit various treatments on a body of a subject such as a patient or the like. The medical device includes an elongated rigid insertion portion and a holder assembly having an articulated arm supports the medical device attached to a tip thereof. The holder assembly is actuated following movement of the medical device and can hold the medical device in a stationary state at a desired position. A position/attitude detection unit detects positions and attitudes of the insertion portion in plurality states into which the medical device has been caused to swing about a predetermined constraint point. A constraint point estimation unit estimates a position of the constraint point on the basis of the positions and attitudes of the insertion portion as detected by the position/attitude detection unit.

According to this aspect, when the insertion portion is constrained from movement at an arbitrary position as a constraint point and the medical device is caused to swing about the constraint point, the holder assembly actuates following movement of the medical device, whereby the medical device can be held in a stationary state at a desired position. Consequently, the observation or treatment of an affected part is performed by controlling the position and attitude of the medical device. In this case, the positions and attitudes of the insertion portion in plurality states caused by swinging of the medical device about the constraint point are detected by the position/attitude detection unit. Based on the detected positions and attitudes, the position of the constraint point is estimated by the constraint point estimation unit. Therefore, even if the constraint point has moved, it is possible to estimate the position of the constraint point and to correct its movement without removing the insertion portion from the constraint point or using any dedicated jig. In the above-described aspect, the position/attitude detection unit may include angle sensors arranged at individual joints of the arm. The position and attitude of the insertion portion in each state is easily detected on the basis of information on angles of the individual joints of the arm as detected by the corresponding angle sensors.

In the above-described aspect, the constraint point may be set at an insertion hole that extends through the body wall of a patient and allows insertion of the insertion portion therethrough. The medical device may include a bending joint at a tip of the insertion portion so as to provide movement in various directions. The medical manipulator system further includes a control unit that controls the bending joint in a state that the bending joint can pass through the insertion hole if a distance between the constraint point and the bending joint is equal to or smaller than a first threshold.

Using the above-described configuration, when the insertion portion of the medical device is inserted into the insertion hole and a proximal end of the medical device is manipulated, then the medical device swings about the position of the insertion hole as a constraint point so that the position and attitude of the insertion portion can be changed. In this manner, if the distance between the estimated constraint point and the bending joint is short, any careless attempt to pull out the insertion portion from the insertion hole with the bending joint being still in a bent state results in the catching of the insertion portion in the insertion hole at a location of the insertion portion toward the tip thereof beyond the bending joint. According to this aspect, if the distance between the constraint point and the bending joint is equal to or smaller than a first threshold, then the control unit controls the bending joint in a state that the bending joint can pass through the insertion hole so that even if a careless attempt is made to pull out the insertion portion, the insertion portion can be pulled out without being caught. The control unit may control the bending joint so that if the distance is greater than the first threshold, the bending joint is provided with a movable range which becomes smaller as the distance decreases. The movable range of the bending joint becomes small as the bending joint is closer to the insertion hole so that even if an attempt is made to pull out the insertion portion in a state that the bending joint is located at a position close to the insertion hole, the bending joint can be more reliably prevented from being caught in the insertion hole.

In the above-described aspect, the constraint point estimation unit may output, as estimated values, temporary position coordinates of the constraint point when a distance between: (i) position coordinates of a predetermined point on the medical device as calculated based on the positions and attitudes of the insertion portion as detected by the position/attitude detection unit and (ii) position coordinates of the predetermined point calculated based on the temporary position coordinates of the constraint point has converged to a second threshold or smaller. When temporary position coordinates of a constraint point are set and a calculation is repeated until the distance between (i) position coordinates of a predetermined point as calculated based on the positions and attitudes of the insertion portion as detected by the position/attitude detection unit and (ii) position coordinates of the predetermined point calculated based on the temporary position coordinates of the constraint point has converged to the second threshold or smaller, whereby estimated values of the constraint point are outputted. In this manner, the control unit may output an error signal if the distance calculated by the constraint point estimation unit fails to converge to a third threshold or smaller. If the convergent calculation for the constraint point fails to converge, an error signal is outputted to enable to notify the operator that the position of the constraint point has moved. The control unit may control the bending joint in the state that the bending joint can pass through the insertion hole if the distance calculated by the constraint point estimation unit is greater than the third threshold.

When configured as described herein, if the convergent calculation for the constraint point fails to converge, then the bending joint is controlled into a state that the bending joint can pass through the insertion hole so that in situation where a careless attempt is made to pull out the insertion portion from the insertion hole, the insertion portion can be pulled out without being caught in the insertion hole at a location of the insertion portion toward the tip beyond the bending joint. The control unit may register position coordinates of a target point for the medical device and may renew the position coordinates of the registered target point on the basis of position coordinates of the constraint points before and/or after the output of the error signal. When configured as described herein, if the convergent calculation for the estimation of the constraint point fails to converge, then the constraint point has moved in a state that the target point for the medical device has been registered. The processing for the target point for the medical device is continued by renewing the position coordinates of the target point based on the position coordinates of the constraint points before and/or after the output of the error signal.

In this aspect, the holder assembly may include actuators that drive the respective joints. The holder assembly may also include a holder control unit that controls the actuators so that the medical device is caused to swing about the constraint point estimated by the constraint point estimation unit. After the constraint point has been estimated by causing the medical device to swing about the constraint point and actuating the individual joints of the holder assembly following the swinging of the medical device, the holder control unit then control the actuators, which drive the individual joints, to allow the medical device to swing so that the estimated constraint point is avoided from moving.

According to the technology disclosed herein, it is possible to bring about an advantageous effect that a movement of an insertion hole relative to reference coordinates of a medical manipulator can be corrected without using any dedicated jig while maintaining an insertion portion of a medical device in a state of being kept inserted in the insertion hole.

As depicted in FIG. 1, the medical manipulator system 1 includes a medical device such as, for example, an endoscope 3 having an elongated rigid insertion portion 2, a holder assembly 4 carrying the endoscope 3 attached to a tip thereof, and a control unit 5 or a first controller that controls the endoscope 3.

The endoscope 3 includes, at a tip portion of the rigid insertion portion 2, a bending joint 6 that can change the direction of a tip face with an unillustrated object lens provided thereon. The endoscope 3 also includes, at a proximal end portion of the insertion portion 2, a drive unit 7 that actuates the bending joint 6. The drive unit 7 is configured such that the power generated at the drive unit 7 is transmitted to a tip of the insertion portion 2 by an unillustrated power transmission member such as a wire. The power actuates the bending joint 6.

The endoscope 3 is configured so that the insertion portion 2 is inserted into an insertion hole 9 formed through the body wall X of a patient, which the tip end of the endoscope 3 is disposed inside the body wall X and the proximal end is disposed outside the body X, respectively.

The holder assembly 4 includes a base 10, a holding part 11 and an arm 12. The base 10 is arranged movably along the floor. The holding part 11 holds the endoscope 3 thereon. The arm 12 has an articulated structure and is arranged between the base 10 and the holding part 11. The arm 12 has freedom of movement, for example, about six degrees-of-freedom. Consequently, the holder assembly 4 is configured so that when an operator manually causes the endoscope 3, to move to a desired position, individual joints are actuated following the movement of the endoscope 3. The holder assembly 4 is configured to hold the endoscope 3 in a stationary state at the position of each point by an unillustrated counter balancer or under frictions at the individual joints. In addition, the holder assembly 4 also includes one or more angle sensors 13, or position/attitude detection unit, at the individual joints, which detect angles of rotation of the individual joints.

The control unit 5 or the first controller includes a position/attitude calculation unit 14, a constraint point estimation unit 15, an endoscope control unit 16, and a notification unit 17 all of which electronically communicate with one another to operate the medical device such as endoscope 3. The position/attitude calculation unit 14, or position/attitude detection unit, calculates the position and attitude of the insertion portion 2 on the basis of output signals from the one or more angle sensors 13. The constraint point estimation unit 15 estimates the coordinates of a constraint point arranged at the position of the insertion hole 9 based on the position and attitude of the insertion portion 2 as calculated by the position/attitude calculation unit 14. The endoscope control unit 16 controls the endoscope 3 based on the position coordinates of the constraint point as estimated by the constraint point estimation unit 15 and the position of the insertion portion 2 as calculated by the position/attitude calculation unit 14. The position/attitude calculation unit 14 calculates the position and attitude of the holding part 11 based on the information on angles of the individual joints as outputted from the one or more angle sensors 13 for the individual joints. The position/attitude calculation unit 14 also calculates the position coordinates of two points, that is, the tip point and proximal end point of the insertion portion 2 of the endoscope 3 held on the holding part 11 based on the calculated position and attitude of the holding part 11.

Figure 2:
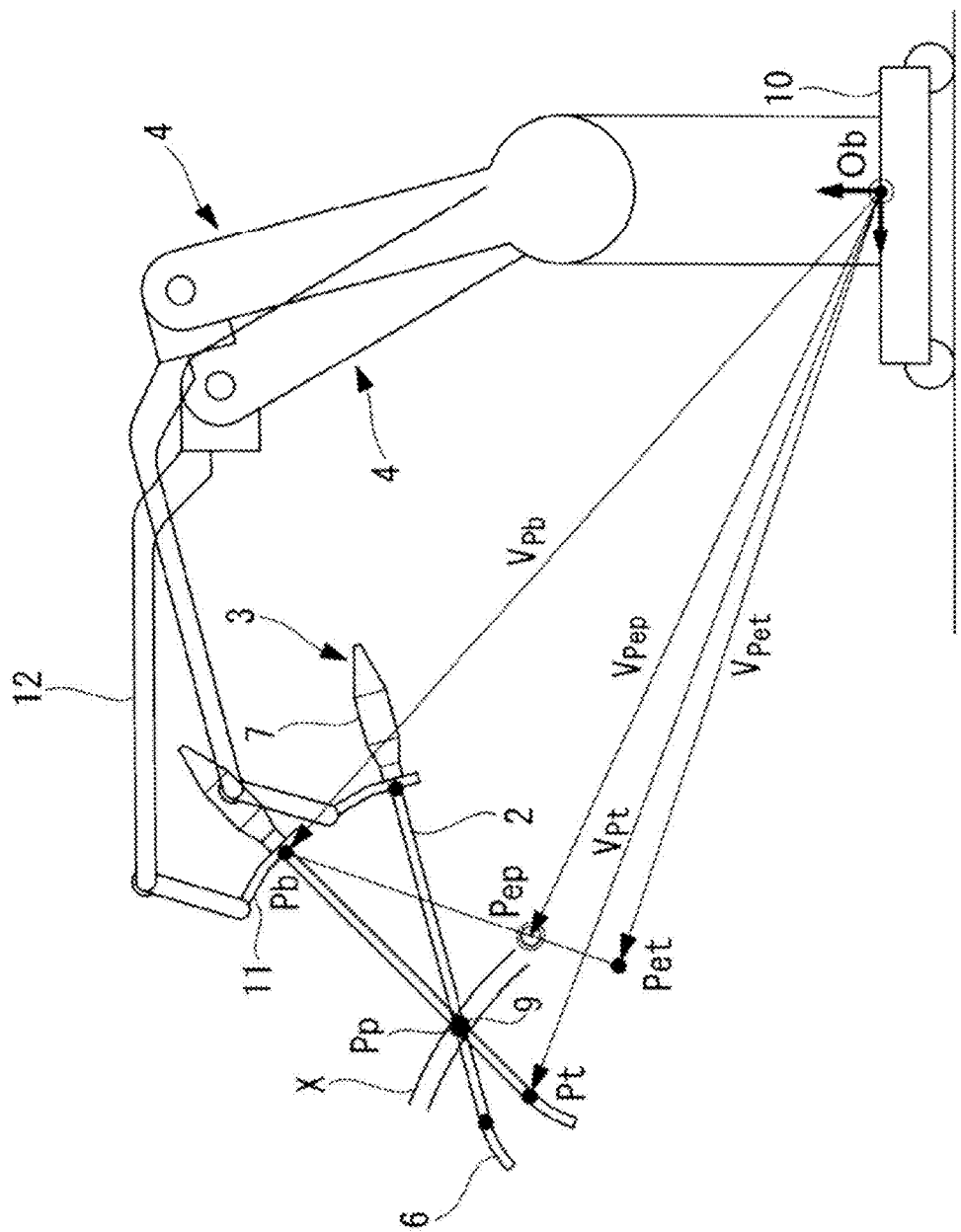
FIG. 2 is a schematic diagram illustrating motions of a medical device and a holder assembly in the medical manipulator system of FIG. 1.

As illustrated in FIG. 2, by calculating the respective position coordinates of the tip point $P_t$ and proximal end point $P_b$ of the insertion portion 2 in two or more different states, the constraint point $P_p$ can be estimated at the intersection of line segments connecting the tip point $P_t$ and the proximal end point $P_b$ in the individual states. The two or more different states are the states in which the insertion portion 2 of the endoscope 3 has been caused to swing about the constraint point set at the insertion hole 9. The constraint point $P_p$ is estimated by the constraint point estimation unit 15 as described hereinafter. A temporary constraint point $P_{ep}$ is set, for example, at an arbitrary point. The position coordinates of a temporary tip point $P_{et}$ is calculated based on the proximal end point $P_b$ and temporary constraint point $P_{ep}$. The position coordinates of the tip point $P_t$ is calculated geometrically from information on angles from the one or more angle sensors 13. If the distance between the position coordinates of a temporary tip point Pet and the position coordinates of the tip point $P_t$ is equal to or smaller than a predetermined threshold, the temporary constraint point $P_{ep}$ is estimated to be the constraint point $P_p$.

Specifically, the temporary tip point $P_{et}$ is calculated from the temporary constraint point $P_{ep}$ in accordance with the following equation (1):

$$V_{Pet} = (V_{Pep} - V_{Pb}) \cdot L / |V_{Pep} - V_{Pb}| \quad (1)$$

where $V_{Pet}$ is a vector directed from a reference position Ob fixed on the base 10 toward the temporary tip point $P_{et}$, $V_{Pep}$ is a vector directed from the reference position Ob toward the temporary constraint point Pep, $V_{Pb}$ is a vector directed from the reference position Ob toward the proximal end point $P_b$, and L is the distance between the tip point $P_t$ and the proximal end point $P_b$.

An evaluation value α is the integrated value of the distance between the temporary tip point Pet and the tip point Pt in plural attitudes of the endoscope 3 in accordance with the following equation (2). The temporary constraint point Pep is estimated as the constraint point $P_p$ when the evaluation value a becomes equal or smaller to a predetermined second threshold $Th_2$:

$$\alpha = \Sigma(V_{Pt} - V_{Pet}) \quad (2)$$

where $V_{Pt}$ means a vector directed from the reference position Ob toward the tip point $P_t$.

The endoscope control unit 16 is configured to calculate the distance between the constraint point and the tip of the insertion portion 2 based on the position coordinates of the constraint point as estimated by the constraint point estimation unit 15 and the position coordinates of the tip of the insertion portion 2 as calculated by the position/attitude calculation unit 14. If the distance between the constraint point and the tip of the insertion portion 2 is equal to or smaller than a predetermined first threshold $Th_1$, then the endoscope control unit 16 controls the bending joint 6 of the endoscope 3. More specifically, if the distance between the tip of the insertion portion 2 and the constraint point, or the insertion hole 9, is short, the bending joint 6 at the tip of the endoscope 3 can readily reach the insertion hole 9 by the operator's pull-out manipulation of the insertion portion 2. In this situation, it is configured that the bending joint 6 is controlled to extend straight along a longitudinal axis of the insertion portion 2.

In the course of the estimation of the constraint point by the constraint point estimation unit 15, there may be a situation that the temporary constraint point is arranged at a position substantially apart from the actual constraint point. In such a situation, the magnitude of the evaluation value α becomes very great. If the evaluation value α calculated by the constraint point estimation unit 15 is greater than a predetermined third threshold $Th_3$, then the constraint point estimation unit 15 delivers an error signal to the notification unit 17 to notify to that effect.

A description will hereinafter be made regarding operations of the medical manipulator system 1 according to this embodiment configured as described hereinbefore.

In order to perform observation or treatment of the affected part of the patient by using the medical manipulator system 1 according to this embodiment, the insertion portion 2 of the endoscope 3 is inserted into the insertion hole 9 formed through the body wall X of the patient. The tip of the endoscope 3 is disposed inside the body and the proximal end of the endoscope 3 is disposed outside the body wall X, as depicted in FIG. 1. The endoscope is held by the holding part 11 provided at the tip of the arm 12 of the holder assembly 4, which is disposed at an appropriate position relative to the patient.

Figure 3:
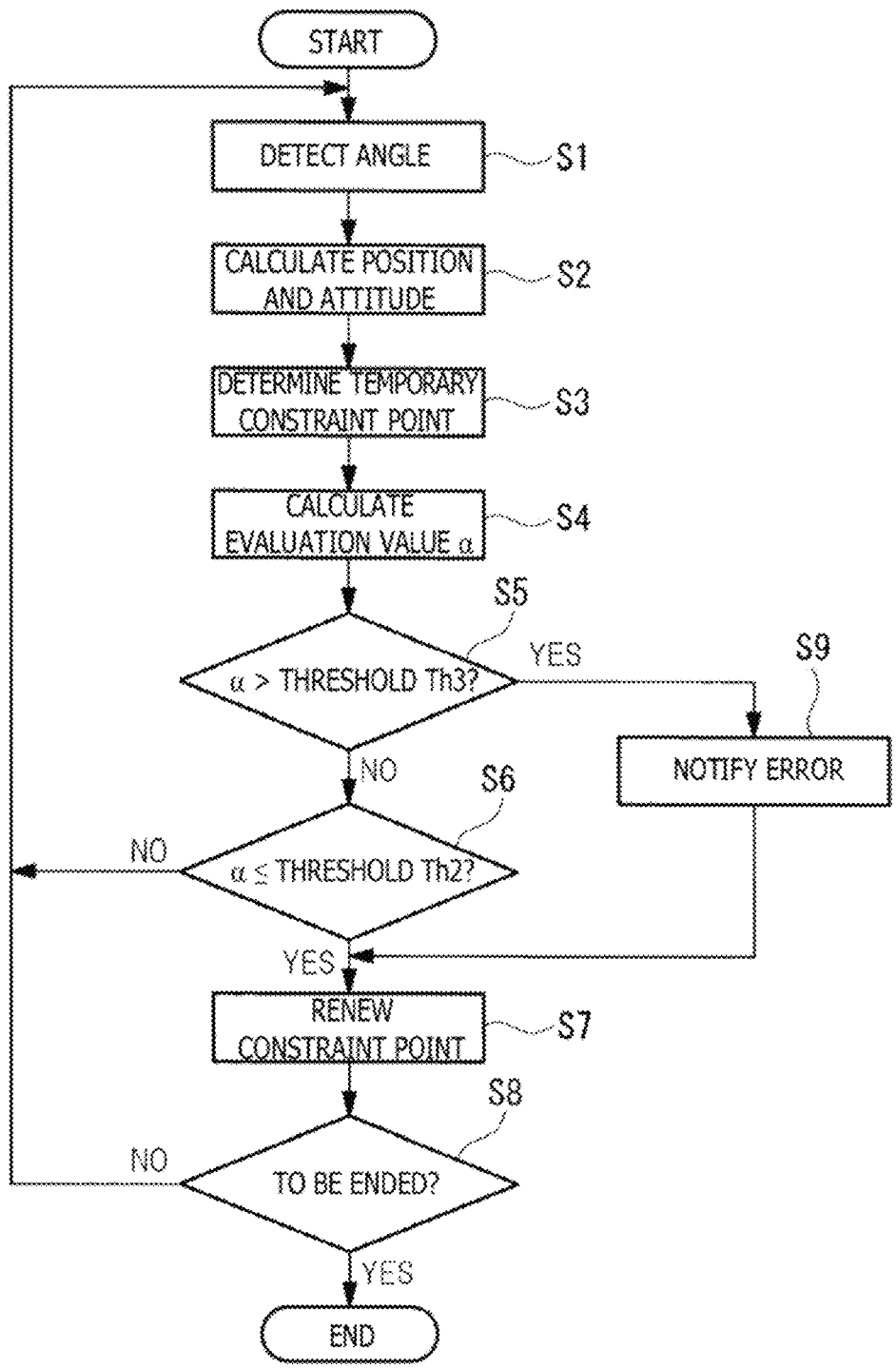
FIG. 3 is a flow chart illustrating estimation procedures for a constraint point by the medical manipulator system of FIG. 1.

When the operator causes the proximal end of the endoscope 3 to move, the proximal end being exposed to the outside of the body wall X, in this state, the insertion portion 2 is caused to swing about the constraint point located at the insertion hole 9 because the insertion portion 2 is constrained at the position of the insertion hole 9 by inserting the insertion portion 2 into the insertion hole 9. Then, the holder assembly 4 causes the individual joints to rotate following the swinging motion of the insertion portion 2 and can hold the insertion portion 2 in a stationary state at each position to which the insertion portion 2 has swung. As illustrated in FIG. 3, the operator then causes the insertion portion 2 to swing about the constraint point, whereby at each position to which the insertion portion 2 has swung, information on angles of the individual joints of the holder assembly 4 is detected by the one or more angle sensors 13 in step S1. Based on the information on the angles so detected, the position and attitude of the insertion portion 2 at each position to which the insertion portion 2 has swung are calculated by the position/attitude calculation unit 14 in step S2. When the positions and attitudes of the insertion portion 2 in two or more states have been calculated, the position coordinates of a temporary constraint point are set by the constraint point estimation unit 15 in step S3.

An evaluation value α is then calculated using the above-described equations (1) and (2) in step S4, and a determination is made as to whether or not the evaluation value α is greater than the threshold $Th_3$ in step S5. If the evaluation value α is greater than the threshold $Th_3$, the constraint point estimation unit 15 outputs an error signal, and a notification is made to that effect to the outside by the notification unit 17 in step S9. If the evaluation value α is equal to or smaller than the threshold $Th_3$, then a determination is made as to whether or not the evaluation value α is equal to or smaller than the threshold $Th_2$ in step S6. If the evaluation value α is greater than the threshold $Th_2$, the steps beginning from step S1 are repeated until the evaluation value α decreases to the threshold $Th_2$ or smaller. If the evaluation value α has decreased to the threshold $Th_2$ or smaller, the position coordinates which have been set as the temporary constraint point are renewed as the position coordinates of the constraint point (step S7). Then, a determination is made as to whether or not the processing is to be ended in step S8. If determined that the processing not to be ended, then the steps beginning from step S1 are repeated.

In this embodiment, once the position coordinates of the constraint point is renewed, the distance between the constraint point and the tip of the insertion portion 2 is calculated using the position coordinates of the constraint point and the position coordinates of the tip. If the distance is equal to or smaller than the first threshold $Th_1$, the endoscope control unit 16 controls the bending joint 6 straight or to allow the bending joint to freely bend following external forces. Therefore, there is a merit in that, even if the insertion portion 2 is carelessly caused to move in a direction that the insertion portion 2 is to be pulled out from the insertion hole 9, the bending joint 6 which is in a bent state can be prevented from being caught in the insertion hole 9. As can be readily appreciated from the foregoing, with the medical manipulator system 1 according to this embodiment, it is possible to estimate the constraint point of the insertion portion 2 even if no dedicated jig is provided for attachment as a replacement for the insertion portion 2 or even if the insertion portion 2 is not removed from the insertion hole 9.

Figure 4:
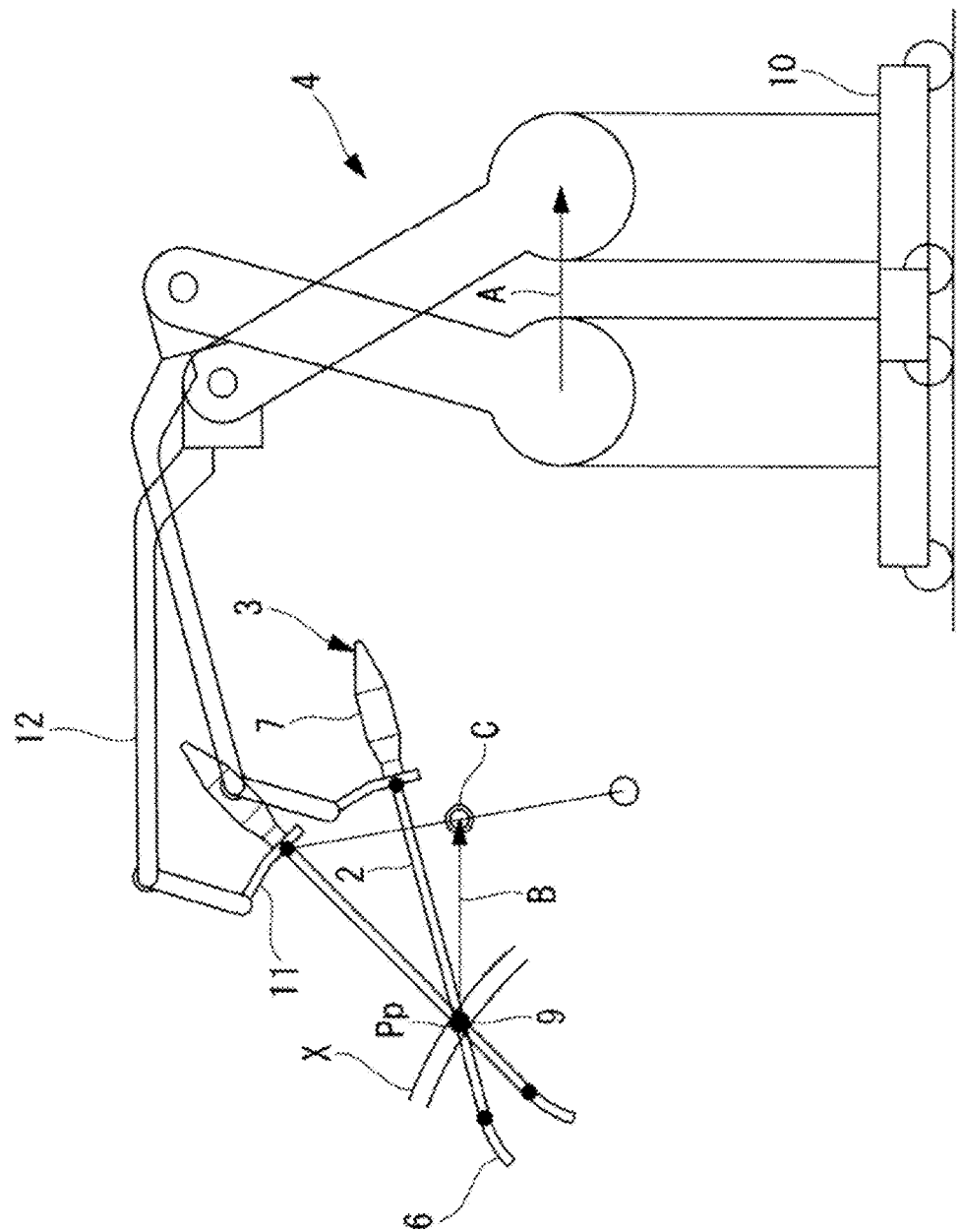
FIG. 4 is a schematic diagram illustrating estimation of a constraint point when a base of the holder assembly moves in the medical manipulator system of FIG. 1.

A description will next be made regarding a situation that the base 10 of the holder assembly 4 has been caused to move as illustrated in FIG. 4. The example of FIG. 4 illustrates the situation that the base 10 has moved in a direction away from the body wall X of the patient, from the left to the right along the sheet as indicated by arrow A in FIG. 4. In this situation, the holder assembly 4 causes the insertion portion 2 of the endoscope 3 to swing about the constraint point set at the actual insertion hole 9, and at the same time, assumes a new attitude by allowing the individual joints to rotate following the swinging. However, the reference coordinate system fixedly set for the base 10 also moves along with the base 10. Therefore, the position coordinates of the constraint point at the control unit 5 also move in the same direction and as much as the displacement of the reference coordinate system as indicated by arrow B in FIG. 4, to a position indicated by sign C.

Figure 5:
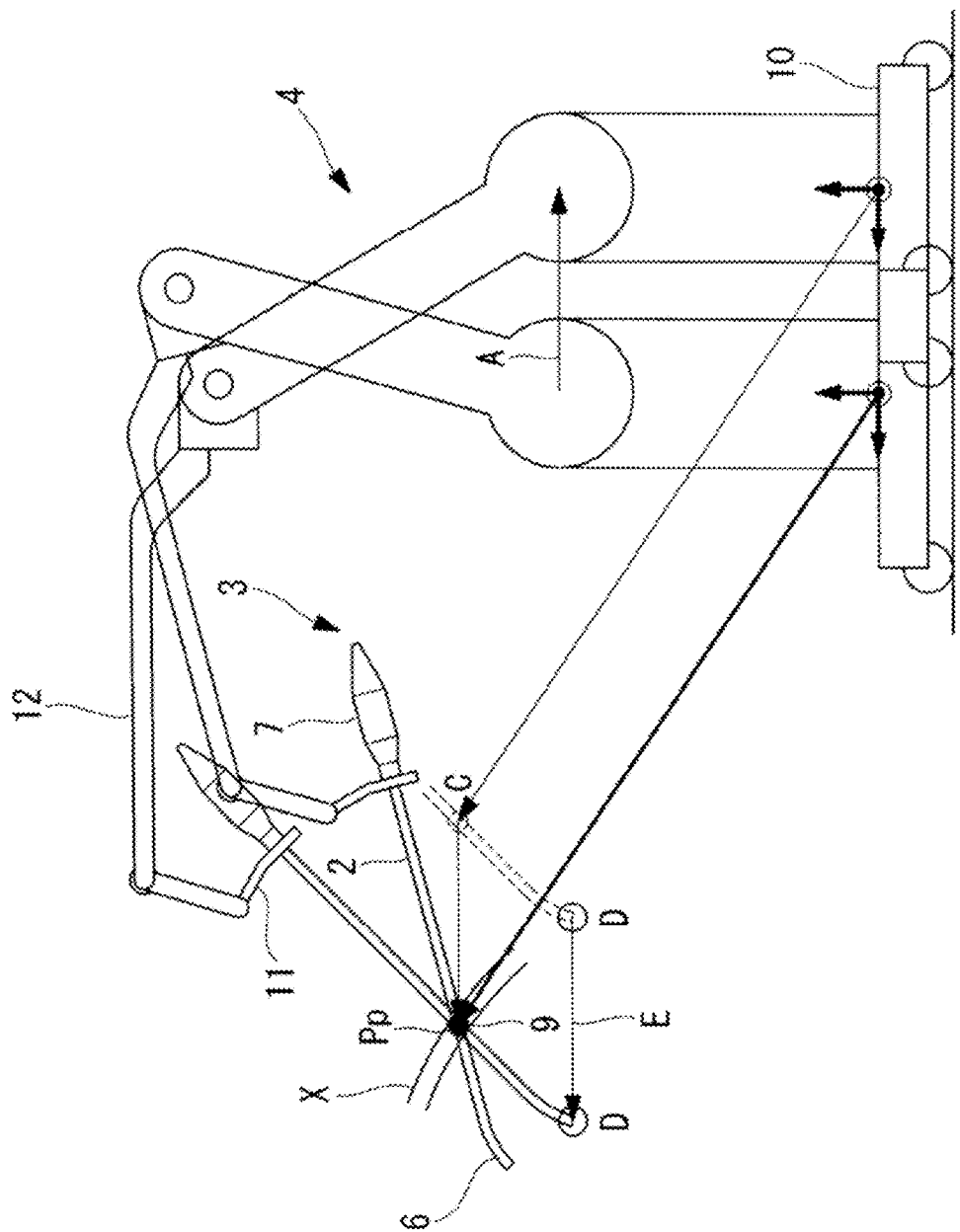
FIG. 5 is a schematic diagram illustrating correction of an arbitrary registration point of the medical device when the base of the holder assembly moves in the medical manipulator system of FIG. 1.

Accordingly, the flow chart of FIG. 3 is executed using the recognized constraint point as a new temporary constraint point. The evaluation value α becomes greater than the threshold $Th_3$, notification of an error signal from step S5 is made in step S9, and the steps beginning from step S1 are repeated. In other words, the operator repeats the operation a plurality of times that the insertion portion 2 is caused to swing about the actual constraint point, whereby the evaluation value α becomes equal to or smaller than the threshold $Th_3$ to end the notification of the error. The true constraint point can be estimated by bringing the temporary constraint point closer to the actual constraint point until the evaluation value α becomes equal to or smaller than the threshold $Th_2$. As can be readily appreciated from the foregoing, with the medical manipulator system 1 according to this embodiment, there is a merit in that, even if the position coordinates of a constraint point as stored relative to a base coordinate system happen to deviate due to movement of the base 10 from any cause during observation or treatment in the body of a patient while using the endoscope 3, the position coordinates of the constraint point can be set again without pulling out the endoscope 3 from the inside of the body or without using any dedicated jig. It is to be noted that the medical manipulator system 1 according to this embodiment may be configured to permit registration of a desired position, for example, the position of the tip D of the endoscope 3 in the reference coordinate system of the base 10. In this configuration, there is a merit in that as illustrated in FIG. 5, even if movement of the reference coordinate system occurs due to movement of the base 10, the registered position coordinates D can be corrected as indicated by arrow E by calculating the displacement and moving direction from the constraint point C before the movement of the base 10 to the constraint point $P_p$ after the movement of the base 10.

Figure 6A:
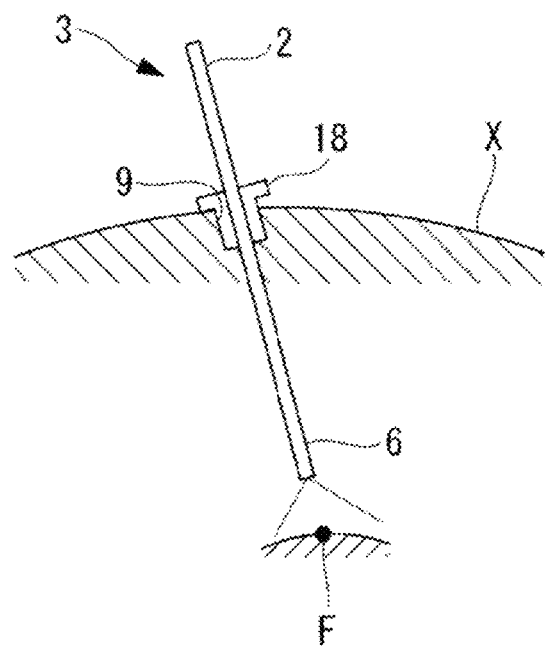
FIG. 6A is a schematic diagram illustrating an example of a registration point set on an observation target in the medical manipulator system of FIG. 1.
Figure 6B:
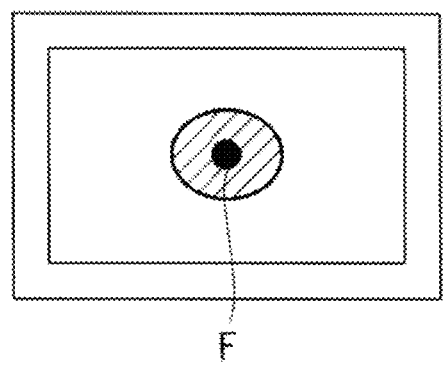
FIG. 6B is a schematic diagram illustrating an example of an image captured by an endoscope of the medical manipulator system of FIG. 6A.
Figure 7A:
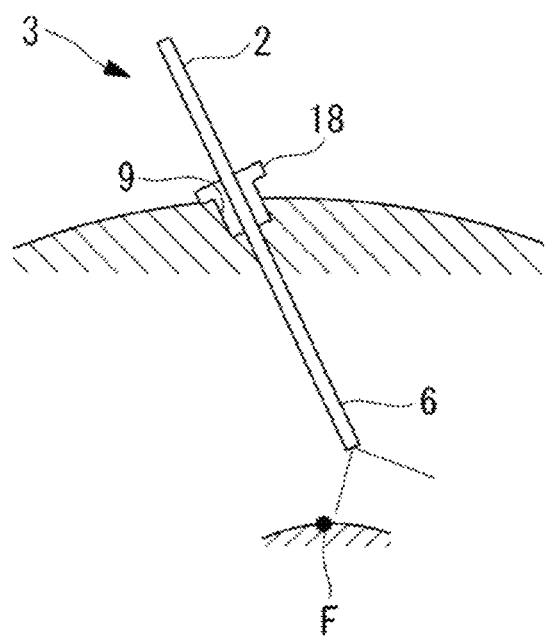
FIG. 7A is a schematic diagram illustrating a situation that the endoscope has swung by movement of the base in the medical manipulator system of FIG. 6A.
Figure 7B:
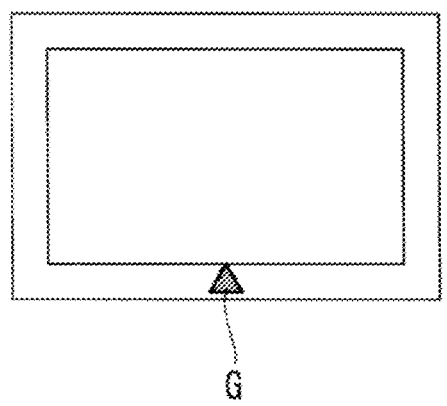
FIG. 7B is a schematic diagram illustrating an example in which a direction instruction has been made to a registration point in an example of an image captured by the endoscope in the situation of FIG. 7A.

As illustrated in FIG. 6A, this embodiment may also be configured to permit, in the reference coordinate system of the base 10, registration of the position coordinates of a desired registration point F as an observation target inside the body of the patient. In the example illustrated in FIG. 6A, the position coordinates of the registration point F that appears in an image of the endoscope 3 is supposed to be registered as illustrated in FIG. 6B. In FIG. 6A, numeral 18 designates a trocar fitted in the insertion hole 9 to facilitate insertion and removal of the insertion portion 2 into and from the insertion hole 9. In this modification, if movement of the reference coordinate system occurs due to movement of the base 10, the endoscope 3 is caused to swing and the registration point F disappears from the image as illustrated in FIG. 7A. However, the registration point F can also be set at the correct position by correcting the registration point F as much as the displacement of the constraint point before and after the movement of the base 10 in a similar manner as described hereinbefore. As a result, as illustrated by way of example in FIG. 7B, a direction indicator mark G can be displayed on the image. The direction indicator mark G indicates the direction in which the registration point F exists even if the registration point F is not appearing on the image. In this embodiment, it is configured to notify an error if the evaluation value $\alpha$ has become greater than the threshold $Th_3$. As an alternative or in addition to the notification of an error, the endoscope control unit 16 may be configured to control the bending joint 6 to extend straight or to be freely bendable following external forces. In this embodiment, the endoscope 3 is exemplified as a medical device, however, as one of ordinary skill in the art would appreciate that other medical devices such as a surgical instrument having the insertion portion 2 may be adopted as well.

In this embodiment, the holder assembly 4 is exemplified as can hold the endoscope 3 in a stationary state at arbitrary positions by causing the individual joints to rotate following movement of the endoscope 3 by the operator. In place of this holder assembly 4, it is possible to adopt one that includes one or more motors or actuators for the individual joints and can control these joints by an unillustrated holder control unit or a second controller. In this modification, the holder control unit or the second controller may be configured to permit selection of a teaching mode of a constraint point or a driving mode after estimation of the constraint point. In the instruction mode, the individual joints are caused to rotate following the operator's operation of the endoscope 3 as in the above-described embodiment. In the driving mode, the individual joints are caused to rotate by actuators (not shown in the drawing) so that the endoscope 3 is caused to swing about the constraint point according to instruction commands from the holder control unit or the second controller. It is configured to detect the position and attitude of the insertion portion 2 by detecting the angles of rotation of the individual joints of the holder assembly 4 with the one or more angle sensors 13. In place of such angle sensors, the position and attitude of the insertion portion 2 may be directly detected by vision sensors or the like from the outside. In this embodiment, the control unit 5 or the first controller may be configured of a single processor, or the position/attitude calculation unit 14, constraint point estimation unit 15, endoscope control unit 16 and notification unit 17 may be configured of separate processors. As an alternative, the control unit 5 or the first controller may be configured of a various desired number of processors as determined by the specific configuration.

In this embodiment, the movable range of the bending joint 6 may be controlled stepwise according to the magnitude of the distance between the constraint point and the tip of the insertion portion 2 if the distance between the constraint point and the tip of the insertion portion 2 is greater than the first threshold $Th_1$. In this modification, it is preferred to make the movable range of the bending joint 6 smaller as the distance between the constraint point and the tip of the insertion portion 2 becomes closer to the first threshold $Th_1$. If the distance between the constraint point and the tip of the insertion portion 2 is sufficiently greater than the first threshold $Th_1$, for example, the movable range of the bending joint 6 may be set at the maximum value. As the distance becomes closer to the first threshold $Th_1$, the movable range may be decreased stepwise or continuously. When configured as described above, the bending joint 6 can bend with a small angle at a position close to the insertion hole 9. Even if the insertion portion 2 is carelessly pulled out from the insertion hole 9, the bending joint 6 can, therefore, be made straight promptly, whereby the insertion portion 2 can be more reliably prevented from being caught in the insertion hole 9. Instead of stepwise control of the bending joint 6, it may be possible to adopt a control unit that continuously controls the angle of rotation of the bending joint 6 according to the distance between the constraint point and the tip of the insertion portion 2.

One aspect of the disclosed technology is directed to a medical manipulator system that comprises a medical device having an elongated insertion portion. A holder assembly having an articulated arm carrying the medical device attached thereto and is actuated following movement of the medical device and holds the medical device in a stationary state at a desired position. A sensor is configured to detect positions and attitudes of the elongated insertion portion in plurality states into which the medical device is caused to swing about a constraint point. A first controller is configured to estimate a position of the constraint point based on the positions and attitudes of the insertion portion as detected by the sensor.

The sensor comprises an angle sensor positioned at a joint of the arm. The constraint point is set at an insertion hole that extends through the body wall of a patient so as to be inserted the elongated insertion portion. The medical device includes a bending joint at a tip of the insertion portion. The first controller is configured to control the bending joint in a state that the bending joint can pass through the insertion hole if a distance between the constraint point estimated by the first controller and the bending joint is equal to or smaller than a first threshold. The first controller is further configured to control the bending joint so that, if the distance is greater than the first threshold, the bending joint having a movable range becomes smaller as the distance decreases. The first controller is configured to calculate a distance between (i) position coordinates of a predetermined point on the medical device as calculated on the basis of the positions and attitudes of the insertion portion as detected by the sensor and (ii) position coordinates of the predetermined point calculated on the basis of the temporary position coordinates of the constraint point; and to output, as estimated values, temporary position coordinates of the constraint point when the distance converged to a second threshold or smaller.

The first controller is configured to output an error signal if the distance fails converge to a third threshold or smaller. The first controller is configured to control the bending joint in the state that the bending joint can pass through the insertion hole if the distance is greater than a third threshold. The first controller is configured to register position coordinates of a target point for the medical device and to renew the position coordinates of the registered target point on the basis of position coordinates of the constraint points before and after the output of the error signal. The holder assembly comprises at least one of an actuator configured to drive the respective joints. The holder assembly comprises a second controller configured to control the actuator so that the medical device is caused to swing about the constraint point estimated by the first controller. The medical device is an endoscope.

Another aspect of the disclosed technology is directed to a medical manipulator system comprises an endoscope having respective proximal end and a free tip end defined by an elongated insertion portion. The elongated insertion portion configured to be inserted into an insertion hole formed through a body of a patient, which the free tip end of the endoscope is disposed inside the body of the patient and the proximal end is disposed outside the body of the patient, respectively. A holder assembly having an articulated arm carrying the endoscope attached thereto and is actuated following movement of the endoscope and holds the endoscope in a stationary state at a desired position. A detection unit detects positions and attitudes of the elongated insertion portion in plurality states into which the endoscope is caused to swing about a constraint point. A constraint point estimation unit estimates a position of the constraint point based on the positions and attitudes of the insertion portion as detected by the detection unit and wherein the medical manipulator system being capable of correcting movement of the insertion hole relative to reference coordinates of the medical manipulator without using any jig while maintaining an insertion portion of the endoscope in a state of being kept inserted in the insertion hole.

The medical manipulator system further comprises a control unit having a calculation unit, the constraint point estimation unit, an endoscope control unit, and a notification unit all of which electronically communicate with one another to operate the endoscope. The endoscope control unit controls the endoscope based on the position coordinates of the constraint point as estimated by the constraint point estimation unit and the position of the insertion portion as calculated by the calculation unit. The holder assembly is configured such that when an operator manually causes the endoscope to move to the desired position, individual joints are actuated following the movement of the endoscope.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical manipulator system comprising:
   a medical device having an elongated insertion portion;
   a holder assembly having an articulated arm carrying the medical device attached thereto and being actuated following movement of the medical device and holds the medical device in a stationary state at a desired position;
   a sensor configured to detect positions and attitudes of the elongated insertion portion in plurality states into which the medical device being caused to swing about a constraint point; and
   a first controller configured to estimate a position of the constraint point based on the positions and attitudes of the elongated insertion portion as detected by the sensor;
   wherein the medical device includes a bending joint at a tip of the elongated insertion portion; and
   the first controller is configured to control the bending joint in a state that the bending joint can pass through the insertion hole if a distance between the constraint point estimated by the first controller and the bending joint is equal to or smaller than a first threshold.

2. The medical manipulator system of claim 1, wherein the sensor comprises an angle sensor positioned at a joint of the arm.

3. The medical manipulator system of claim 1, wherein the constraint point is set at an insertion hole that extends through the body wall of a patient so as to be inserted the elongated insertion portion.

4. The medical manipulator system of claim 1, wherein the first controller is further configured to control the bending joint so that, if the distance is greater than the first threshold, a movable range of the bending joint becomes smaller as the distance decreases.

5. The medical manipulator system of claim 1, wherein the first controller is configured:
  to calculate a distance between
    (i) position coordinates of a predetermined point on the medical device as calculated on the basis of the positions and attitudes of the elongated insertion portion as detected by the sensor and
    (ii) position coordinates of the predetermined point calculated on the basis of temporary position coordinates of the constraint point; and
  to output, as estimated values, the temporary position coordinates of the constraint point when the distance converged to a second threshold or smaller.

6. The medical manipulator system of claim 1, wherein the first controller is configured to output an error signal if the distance fails converge to a third threshold or smaller.

7. The medical manipulator system of claim 6, wherein the first controller is configured to control the bending joint in the state that the bending joint can pass through the insertion hole if the distance is greater than the third threshold.

8. The medical manipulator system of 6, wherein the first controller is configured to:
  register position coordinates of a target point for the medical device, and
  renew the position coordinates of the registered target point on the basis of position coordinates of the constraint points before and after the output of the error signal.

9. The medical manipulator system of claim 1, wherein the medical device is an endoscope.

10. A medical manipulator system comprising:
  a medical device having an elongated insertion portion;
  a holder assembly having an articulated arm carrying the medical device attached thereto and being actuated following movement of the medical device and holds the medical device in a stationary state at a desired position;
  a sensor configured to detect positions and attitudes of the elongated insertion portion in plurality states into which the medical device being caused to swing about a constraint point; and
  a first controller configured to estimate a position of the constraint point based on the positions and attitudes of the elongated insertion portion as detected by the sensor;
  wherein the first controller is configured to:
  calculate a distance between:
    (i) position coordinates of a predetermined point on the medical device as calculated on the basis of the positions and attitudes of the elongated insertion portion as detected by the sensor and
    (ii) position coordinates of the predetermined point calculated on the basis of temporary position coordinates of the constraint point; and
  output, as estimated values, the temporary position coordinates of the constraint point when the distance converged to a second threshold or smaller.

* * * * *